US005985267A

United States Patent [19]

Payne et al.

[11] Patent Number: 5,985,267

[45] **Date of Patent: *Nov. 16, 1999**

[54] PROTEIN TOXINS ACTIVE AGAINST LEPIDOPTERAN PESTS

[75] Inventors: Jewel Payne, San Diego; August J. Sick, Oceanside; Kenneth E. Narva; H. Ernest Schnepf, both of San Diego; George E. Schwab, Encinitas, all of Calif.

[73] Assignee: Mycogen Corporation, San Diego, Calif.

[ * ] Notice: This patent is subject to a terminal disclaimer.

[21] Appl. No.: 08/962,190

[22] Filed: Oct. 31, 1997

Related U.S. Application Data

[63] Continuation of application No. 08/291,368, Aug. 15, 1994, Pat. No. 5,686,069, which is a continuation-in-part of application No. 08/032,778, Mar. 16, 1993, abandoned, which is a continuation of application No. 07/597,607, Oct. 15, 1990, abandoned.

[51] Int. Cl.[6] .......................... A01N 63/00; A01N 63/02; C07K 14/325

[52] U.S. Cl. .................................... 424/93.461; 435/69.1; 435/71.3; 435/252.3; 435/252.31; 435/320.1; 530/350; 424/93.2; 514/12; 536/23.1; 536/23.71

[58] Field of Search ................................ 435/69.1, 71.3, 435/172.3, 252.3, 252.31, 320.1; 530/350; 424/93.2, 93.461; 514/12; 536/23.1, 23.71

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 4,797,276 | 1/1989 | Herrstadt et al. | 424/84 |
| 4,853,331 | 8/1989 | Herrstadt et al. | 435/252.3 |
| 5,151,363 | 9/1992 | Payne | 435/252.5 |
| 5,164,180 | 11/1992 | Payne et al. | 424/93.461 |

FOREIGN PATENT DOCUMENTS

| | | |
|---|---|---|
| 0 405 810 | 1/1991 | European Pat. Off. . |
| 9116434 | 10/1991 | WIPO . |
| 9314641 | 8/1993 | WIPO . |
| 9502694 | 1/1995 | WIPO . |

OTHER PUBLICATIONS

Chambers, J.A. et al. (1991) "Isolation and Characterization of a Novel Insecticidal Crystal Protein Gene from *Bacillus thuringiensis* subsp. aizawai" Journal of Bacteriology 173(13):3966–3976.

Lambert, B. (1993) EMBL Database Entry BTCRYPRTD: Accession number Z22512, Apr. 8, 1993 (see abstract).

Gaertner, F., L. Kim (1988) "Current Applied Recombinant DNA Projects" TIBTECH 6(4):S4–S6.

Gaetner, F. (1990) "Cellular Delivery Systems for Insecticidal Proteins: Living and Non–Living Microorganisms" Controlled Delivery of Crop–Protection Agents 12:245–257.

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems" Developments in Industrial Microbiology 20:97–104.

Krieg, V.A. et al. (1983) "*Bacillus thuringiensis*var. *tenebrionis*: ein neuer, gegnuber Larven von von Coleopteran wirksamer Pathotyp" Z. Ang. Ent. 96:500–508.

Hofte, H., H.R. Whiteley (1989) "Insecticidal Crystal Proteins of *Bacillus thuringiensis*" Microbiological Reviews 53(2):242–255.

Feitelson, J.S. et al. (1992) "*Bacillus thuringiensis*: Insects and Beyond" Bio/Technology 10:271–275.

Schnepf, H.E., H.R. Whiteley (1981) "Cloning and Expression of the *Bacillus thuringiensis* Crystal Protein Gene in *Eschrichia coli*" Proc. Natl. Acad. Sci. USA 78(5):2893–2897.

*Primary Examiner*—Rebecca E. Prouty
*Attorney, Agent, or Firm*—Saliwanchik, Lloyd & Saliwanchik

[57] ABSTRACT

Disclosed and claimed are novel *Bacillus thuringiensis* isolates which have lepidopteran activity. Thus, these isolates, or mutants thereof, can be used to control such insect pests. Further, genes encoding novel δ-endotoxins can be removed from the isolates and transferred to other host microbes, or plants. Expression of the δ-endotoxins in such hosts results in the control of susceptible insect pests in the environment of such hosts.

5 Claims, 1 Drawing Sheet

```
1
MjNNIQNQCV PYNCLxNPEV EILxEERSTG RLPLDISLSL TRFLLSEFVP
GVGVAFGLFD LIWGFITPSx WSLFLLQIEQ LIEQRIETLE RNRAITTLRG
LADSYEbYbE ALREWE-NPN NAQLREDVRI RFANTDDALI TAINNFTLTS
FEIPLLSVYV QAANLHLSLL RDAVSFGQGW GLDIATVNNH YNRLINLIHR

201
YTjHCLDTYN QGLENLRGTN TRQW-RFNQF RRxLTLTVLD IVALFPNYDo
RuYPIQTSSQ LTREIYTSSV IEDSPVSANI PNGFNRAEFG VRPPHLMDFM
NSLFVTAETV RSQTVWGGHL VSSRNTAGN- INFP.YGVFN PGGAIWIADE
DPRPFYRTLS DPVFVRGGFG zPHYVLGLRG V-FQQTGTNH TRTFRNSGTI

401
DSLDEIPPQD NSGAPWNDYS HVLNHVTFVR WPGEI-GSDS WRAPMFSWTH
RSA--TNoIz Px-ITQIPoV KAH-L-SG-T VVRGPGFTGG DbLRRTz-Go
FA-o-VNI-G -L-QRYRoRI RYASTTzLjb -o-b-G-xb- -GxFxkTMx-
GD-L--xzFx -A-bzToF-F ---QS-FTbG uxuF.SzxEV YIDkbEbbPo

601
-oTFEAE-DK ERAQKAVNAL FTSozQbGbK TzVTzYHIDQ VSNLV-CLSD
EFCLDEKREL SEKVHKAKRL SDxRNLLQDP NFkGINRQoD -GWRGSTDIT
IQxGDDVFKE NYVTLPGTFD ECYPTYLYQK IDESKLK-YT RYQLRGYIED
SQDLEIYLIR YN-KHEpVNV oGTGSLWPLS Vjz-Ix-CGE PNRCAPHLEW

801
NPDL-CSCRD GEKCoHHSHH FSLDIDVGCT DLNEDLzVWb IFKIKTQDGH
ARLGNLEFLE EjPLbGEAL- RVKRAEKKWR DKREKLjLET NIVYKEAKES
VDALFVNSQY DjLQADTNIA MIHAADKRVH RIREAYLPEL SVIPGVNo-I
FEELjGRIFT A--LYDARNV IKNGzFNNGL -CWNVKGHVD VEEQNNHRSV

1001
LVVPEWEAEV SQEVRVCPGR GYILRVTAYK EGYGEGCVTI HEbxNNTDEL
KFSNC-xEjV YPzNTVuCND Y--N-X..-Z A--SRNRGYD E-YxSNSSbP
ADYA-VYEEj -YTDGjRzNP CE-NRG...- TPLPAGYVT- ELEYFPETD-
VWbEIGETEG TFIVDSVELL LMEE
```

FIG. 1

PROTEIN TOXINS ACTIVE AGAINST LEPIDOPTERAN PESTS

CROSS-REFERENCE TO A RELATED APPLICATION

This is a continuation of application Ser. No. 08/291,368, filed Aug. 15, 1994 now U.S. Pat. No. 5,686,069 which is a continuation-in-part of application Ser. No. 08/032,778, filed Mar 16, 1993 now abandoned, which is a continuation of application Ser. No. 07/597,607, filed Oct. 15, 1990, now abandoned.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. These crystalline proteins can be proforms of δ-endotoxins which are highly toxic to pests and specific in their toxic activity. Certain *B.t.* endotoxin genes have been isolated and sequenced, and recombinant DNA-based *B.t.* products have been produced and approved. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH* 6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B.thuringiensis* subsp. *kurstaki* have been used for many years as commercial insecticides for lepidopteran pests. For example, *B.thuringiensis* var. *kurstaki* HD-1 produces a delta endotoxin which is toxic to the larvae of a number of lepidopteran insects.

In recent years, however, investigators have discovered *B.t.* pesticides with specificities for a much broader range of pests. For example, subspecies of *B.t.*, namely *israelensis* and *san diego* (a.k.a. *B.t.* tenebrionis, a.k.a. M-7), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents,* R. M. Wilkins, ed., Taylor and Francis, New York and London, 1990, pp. 245–255). See also Couch, T. L. (1980) "Mosquito Pathogenicity of *Bacillus thuringiensis* var. *israelensis," Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent* 96:500–508, describe a *B.t.* isolate named *Bacillus thuringiensis* var. *tenebrionis,* which is reportedly active against two beetles in the order Coleoptera. These are the Colorado potato beetle, *Leptinotarsa decemlineata,* and *Agelastica alni.*

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific),CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] Bio/Technology 10:271–275).

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli.* U.S. Pat. Nos. 4,797,276 and 4,853,331 disclose *B.thuringiensis* var. *san diego* (a.k.a. *B.t.* tenebrionis, a.k.a. M-7) which can be used to control coleopteranpests in various environments. U.S. Pat. No. 5,164,180 discloses a *B.t.* isolate, PS81A2, which is active against lepidopteran pests. U.S. Pat. No. 5,151,363 discloses certain isolates of *B.t.* which have activity against nematodes. Many other patents have issued for new *B.t.* isolates and new uses of *B.t.* isolates. The discovery of new *B.t.* isolates and new uses of known *B.t.* isolates remains an empirical, unpredictable art.

BRIEF SUMMARY OF THE INVENTION

The subject invention concerns novel *Bacillus thuringiensis* isolates which have activity against lepidopteran pests.

Specifically, the invention comprises novel *B.t.* isolates and mutants thereof, and novel delta endotoxin genes obtainable from these *B.t.* isolates which encode proteins which are active against lepidopteran pests.

BRIEF DESCRIPTION OF THE DRAWING

FIG. 1 shows the one-letter amino acid sequence of the Generic Formula (SEQ ID NO. 27). Numbering is for convenience and approximate location only. In the Generic Formula, the N-terminal half of the molecule is comprised of residue nos. 1–638. The terminal half is comprised of residues 639–1213. Wherein

| | | | |
|---|---|---|---|
| A = ala | G = gly | M = met | S = ser |
| C = cys | H = his | N = asn | T = thr |
| D = asp | I = ile | P = pro | V = val |
| E = glu | K = lys | Q = gln | W = trp |
| F = phe | L = leu | R = arg | Y = tyr |
| k = K or R | | | |
| z = G, S, D, or N | | | |
| j = E, Q, R, or K | | | |
| x = G, S, D, N, E, Q, R, or K | | | |
| u = C, P, T, or A | | | |
| b = M, I, L, V, or F | | | |
| o = C, P, T, A, M, I, L, V, or F | | | |

- = any naturally occurring amino acid
. = any naturally occurring amino acid or complete omission thereof.

BRIEF DESCRIPTION OF THE SEQUENCES

SEQ ID NO. 1 is the nucleotide sequence of the gene 81A2.

SEQ ID NO. 2 is the amino acid sequence of the toxin 81A2.

SEQ ID NO. 3 is the nucleotide sequence of the gene 91C2.

SEQ ID NO. 4 is the amino acid sequence of the toxin 91C2.

SEQ ID NO. 5 is a radiolabeled oligonucleotide probe used in RFLP analysis as described in Example 3.

SEQ ID NO. 6 is a forward oligonucleotide primer used to amplify gene 91C2 according to the subject invention.

SEQ ID NO. 7 is a reverse oligonucleotide primer used to amplify gene 91C2 according to the subject invention.

SEQ ID NO. 8 is a synthetic oligonucleotide probe used to identify gene 91C2 according to the subject invention.

SEQ ID NO. 9 is the peptide sequence encoded by probes for CryIF genes.

SEQ ID NO. 10 is a nucleotide probe according to the subject invention.

SEQ ID NO. 11 is the peptide sequence encoded by probes for CryIF genes.

SEQ ID NO. 12 is a nucleotide probe according to the subject invention.

SEQ ID NO. 13 is the peptide sequence encoded by probes for CryIF genes.

SEQ ID NO. 14 is a nucleotide probe according to the subject invention.

SEQ ID NO. 15 is the peptide sequence encoded by probes for CryIF genes.

SEQ ID NO. 16 is a nucleotide probe according to the subject invention.

SEQ ID NO. 17 is the peptide sequence encoded by probes for CryIF genes.

SEQ ID NO. 18 is a nucleotide probe according to the subject invention.

SEQ ID NO. 19 is the peptide sequence encoded by probes for CryIF genes.

SEQ ID NO. 20 is a nucleotide probe according to the subject invention.

SEQ ID NO. 21 is the peptide sequence encoded by probes for CryIF genes.

SEQ ID NO. 22 is a nucleotide probe according to the subject invention.

SEQ ID NO. 23 is the peptide sequence encoded by probes for CryIF genes.

SEQ ID NO. 24 is a nucleotide probe according to the subject invention.

SEQ ID NO. 25 is the peptide sequence encoded by probes for CryIF genes.

SEQ ID NO. 26 is a nucleotide probe according to the subject invention.

SEQ ID NO. 27 is the Generic Formula according to the subject invention.

DETAILED DISCLOSURE OF THE INVENTION

The subject invention concerns isolates of *Bacillus thuringiensis* having anti-lepidopteran activity. These isolates comprise genes which code for δ-endotoxins, which toxins are responsible for the observed anti-lepidopteran activity. Thus, the subject invention concerns anti-lepidopteran *B.t.* isolates, anti-lepidopteran *B.t.* toxins, and genes which encode these toxins. Further embodiments of the subject invention concern recombinant hosts transformed with genes encoding the anti-lepidopteran *B.t.* toxins.. The subject invention further concerns methods for controlling lepidopterans, said methods comprising the use of the isolates, toxins, genes, and recombinant hosts of the subject invention.

Specifically exemplified herein are the isolates designated *B.t.* PS81T1, *B.t.* PS53C2, *B.t.* PS31F4, *B.t.* PS86V1, *B.t.* PS 8612, *B.t.* PS73E, *B.t.* PS81K, *B.t.* PS83E2, *B.t.* PS81E, *B.t.* PS81Z3, *B.t.* PS53B5, *B.t.* PS83R, *B.t.* PS53B2, Bt. PS83N2, *B.t.* PS81B5, *B.t.* PS86W1, and *B.t.* PS93C2. Also specifically exemplified is the toxin designated 91C2 and the gene which encodes this toxin. The 91C2 gene is a CryIF gene. CryIF is a subclass of genes within the lepidopteran-active CryI class of *B.t.* genes. The discovery described in the subject application enables a person skilled in the art to identify other CryIF toxins (and genes coding for these toxins) having anti-lepidopteran activity. The toxins of the subject invention are characterized as being active against lepidopterans and having one or more of the following characteristics:

1. A high degree of amino acid homology with toxin 91C2.
2. A nucleotide sequence encoding the toxin wherein the nucleotide sequence hybridizes with probes or genes disclosed herein.
3. A nucleotide sequence encoding the toxin wherein the nucleotide sequence can be amplified by PCR using primers disclosed herein.
4. An amino acid sequence which conforms to the Generic Formula presented herein.
5. Immunoreactivity to an antibody raised to toxin 91 C2.

*Bacillus thuringiensis* isolates useful according to the subject invention have the following characteristics in their biologically pure form:

TABLE 1

Taxonomic characterization of the *B.t.* isolates of the subject invention

| Isolate | Crystal Type | Approx. Toxin MW (kD) | Serotype | Activity |
|---|---|---|---|---|
| PS81T1 | bipyramid | 130 | aizawai | Lepidoptera |
| PS53C2 | bipyramid | 130, 60 | kurstaki | Lepidoptera |
| PS31F4 | bipyramid | 130, 60 | kurstaki | Lepidoptera |
| PS86V1 | bipyramid | 130 | galleriae | Lepidoptera |
| PS86I2 | bipyramid | 130 | morrisoni | Lepidoptera |
| PS73E | bipyramid | 130 | aizawai | Lepidoptera |
| PS81K | bipyramid | 130 | aizawai | Lepidoptera |
| PS83E2 | amorphic | 130 | aizawai | Lepidoptera |
| PS81E | bipyramid | 130 | aizawai | Lepidoptera |
| PS81Z3 | bipyramid | 130 | aizawai | Lepidoptera |
| PS53B5 | bipyramid | 130, 60 | kenyae | Lepidoptera |
| PS83R | bipyramid | 130 | aizawai | Lepidoptera |
| PS53B2 | bipyramid | 130, 60 | kenyae | Lepidoptera |
| PS83N2 | bipyramid | 130, 60 | sotto/kenyae | Lepidoptera |
| PS81B5 | amorphic | 130 | aizawai | Lepidoptera |
| PS86W1 | bipyramid | 130 | galleriae | Lepidoptera |
| PS91C2 | bipyramid | 130 | morrisoni | Lepidoptera |

*B.t.* isolates useful according to the subject invention have been deposited. Also deposited are recombinant microbes comprising the *B.t.* genes of interest. The cultures have been deposited in the permanent collection of the Patent Culture Collection (NRRL), Regional Research Center, 1815 North University Street, Peoria, Ill. 61604 USA.

| Culture | Accession Number | Deposit Date |
|---|---|---|
| *Bacillus thuringiensis* PS81IA | NRRL B-18484 | April 19, 1989 |
| *Bacillus thuringiensis* PS91C2 | NRRL B-18931 | December 27, 1991 |
| *E. Coli* NM522 (pMYC2361) | NRRL B-21016N | December 17, 1992 |

The subject cultures have been deposited under conditions that assure that access to the cultures will be available during the pendency of this patent application to one determined by the Commissioner of Patents and Trademarks to be entitled thereto under 37 CFR 1.14and 35 U.S.C. §122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

Toxins and genes. The toxins and genes according to the subject invention include not only the full length sequences disclosed herein but also fragments of these sequences, longer sequences, and fusion proteins, which retain the characteristic pesticidal activity of the toxins specifically exemplified herein.

One aspect of the subject invention concerns the discovery of a generic chemical formula hereinafter referred to as the Generic Formula (SEQ ID NO.27), which can be used to identify toxins having activity against lepidopterans. The Generic Formula describes toxin proteins having molecular weights of about 130 kDa.

The Generic Formula is shown in FIG. 1 designated by a one-letter amino acid sequence. The Sequence Listing provided herein according to the PatentIn format utilizes the three-letter amino acid code and has no provision for showing a choice between two amino acids at a given position. Therefore, within the PatentIn Sequence Listing, "Xaa" is used to denote points of variation within a sequence, but the single letter code of FIG. 1 should be referred to for the specific amino acid substitutions which are acceptable at a given location in the sequence.

Further guidance for characterizing the lepidopteran toxins of the subject invention is provided in Tables 2 and 3, which demonstrate the relatedness among toxins within the known CryI subclasses of lepidopteran toxins. These tables show a numeric score for the best matching alignment between two proteins that reflects: (1) positive scores for exact matches, (2) positive or negative scores reflecting the likelihood (or not) of one amino acid substituting for another in a related protein, and (3) negative scores for the introduction of gaps. A protein sequence aligned to itself will have the highest possible-score, i.e., all exact matches and no gaps. However, an unrelated protein or a randomly generated sequence will typically have a low positive score. Related sequences have scores between the random background score and the perfect match score.

The sequence comparisons reported herein were made using the algorithm of Smith and Waterman ([1981] *Advances in Applied Mathematics* 2:482–489), implemented as the program "Bestfit" in the GCG Sequence Analysis Software Package Version 7, April 1991. The sequences were compared with default parameter values (comparison: Swagappep.Cmp, Gap: 3.0, length weight: 0.1). The program output value is referred to as the Quality score.

Tables 2 and 3 show the pairwise alignment scores between the indicated amino acids of the CryI toxin proteins. Table 4 shows the amino acids compared from the proteins of interest.

Table 2 shows the scores prior to adjustment for random sequence scores. Note that for each subclass, the highest alignment score is always with another toxin protein from the same subclass. For example, the highest alignment score with CryIA(a), aside from itself, is with CryIA(d). Furthermore, CryIA(a) scores highest with all three other CryIA toxin proteins. In a similar manner, other CryI toxins score highest with other members of the same subclass. Of particular relevance to the subject invention is the fact that the CryIF toxin proteins score highest with each other.

Table 3 shows the same analysis after subtraction of the average score of 50 alignments of random shuffles of the column sequences with the row sequences. Note that in Table 3 the same relationships hold as in Table 2, i.e., toxin proteins score highest with other members of the same subclass. Again, the two CryIF toxin proteins score highest with each other. Examination of the adjusted alignment scores for members of the same subclass reveals that CryI subclasses can be defined as those proteins with adjusted alignment scores of about 450 or greater.

Thus, certain toxins of the subject invention can be defined as those which have lepidopteran activity and have an alignment value of 450–500 or greater with CryIF(a) or CryIF(b) (91C2). As used herein, the term "alignment value" refers to the adjusted scores obtained above and used to create the scores reported in Table 3.

TABLE 2

| | Raw quality scores | | | | | | | | | | |
|---|---|---|---|---|---|---|---|---|---|---|---|
| | CryIA(a) | CryIA(b) | CryIA(c) | CryIA(d) | CryIB | CryIC | CryID | CryIE(a) | CryIE(b) | CryIF(a) | CryIF(b) (91C2) |
| CryIA(a) | 911 | 819 | 706 | 857 | 426 | 519 | 533 | 536 | 535 | 532 | 557 |
| CryIA(b) | | 912 | 785 | 790 | 428 | 512 | 540 | 547 | 546 | 543 | 565 |
| CryIA(c) | | | 914 | 679 | 390 | 482 | 508 | 512 | 533 | 502 | 501 |
| CryIA(d) | | | | 911 | 422 | 514 | 539 | 549 | 538 | 539 | 559 |
| CryIB | | | | | 954 | 428 | 410 | 408 | 375 | 421 | 434 |
| CryIC | | | | | | 926 | 525 | 547 | 480 | 494 | 495 |
| CryID | | | | | | | 888 | 505 | 499 | 507 | 497 |
| CryIE(a) | | | | | | | | 902 | 722 | 494 | 487 |
| CryIE(b) | | | | | | | | | 899 | 480 | 477 |
| CryIF(a) | | | | | | | | | | 902 | 803 |
| CryIF(b) (91C2) | | | | | | | | | | | 900 |

TABLE 3

| | Net quality scores | | | | | | | | | | |
|---|---|---|---|---|---|---|---|---|---|---|---|
| | CryIA(a) | CryIA(b) | CryIA(c) | CryIA(d) | CryIB | CryIC | CryID | CryIE(a) | CryIE(b) | CryIF(a) | CryIF(b) (91C2) |
| CryIA(a) | 724 | 633 | 520 | 671 | 240 | 332 | 352 | 351 | 350 | 349 | 373 |
| CryIA(b) | | 726 | 600 | 606 | 241 | 327 | 359 | 362 | 360 | 360 | 383 |
| CryIA(c) | | | 728 | 493 | 204 | 295 | 327 | 328 | 347 | 319 | 317 |
| CryIA(d) | | | | 727 | 236 | 328 | 357 | 363 | 353 | 356 | 377 |
| CryIB | | | | | 763 | 240 | 229 | 223 | 189 | 235 | 249 |
| CryIC | | | | | | 738 | 343 | 361 | 293 | 309 | 309 |
| CryID | | | | | | | 710 | 325 | 319 | 328 | 318 |
| CryIE(a) | | | | | | | | 717 | 538 | 310 | 304 |
| CryIE(b) | | | | | | | | | 713 | 296 | 294 |
| CryIF(a) | | | | | | | | | | 719 | 620 |
| CryIF(b) (91C2) | | | | | | | | | | | 713 |

TABLE 4

| Protein | Amino acids compared |
|---|---|
| CryIA(a) | 1-607 |
| CryIA(b) | 1-608 |
| CryIA(c) | 1-609 |
| CryIA(d) | 1-607 |
| CryIB | 1-636 |
| CryIC | 1-617 |
| CryID | 1-592 |
| CryIE(a) | 1-601 |
| CryIE(b) | 1-599 |
| CryIF(a) | 1-601 |
| CryIF(b) (91C2) | 1-600 |

Toxins of the subject invention are specifically exemplified herein by the toxin encoded by the gene designated 91C2. Since this toxin is merely exemplary of the toxins of the subject invention, it should be readily apparent that the subject invention further comprises variant toxins (and nucleotide sequences coding for variant toxins) having the same, or essentially the same, biological activity against lepidopterans of 91C2. These equivalent toxins will have amino acid homology with 91C2. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be readily made in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 5 provides a listing of examples of amino acids belonging to each class.

TABLE 5

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

It should be apparent to a person skilled in this art that genes encoding lepidopteran-active toxins can be identified and obtained through several means. The specific genes exemplified herein may be obtained from the isolates deposited at a culture depository as described above. These genes, or portions or variants thereof, may also be constructed synthetically, for example, by use of a gene machine. As used herein, the terms "variants" or "variations" of genes refer to nucleotide sequences which code for the same toxins or which code for equivalent toxins having lepidopteran activity. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be located from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are detectable nucleotide sequences. These sequences may be detectable by virtue of an appropriate label or may be made inherently fluorescent as described in International Patent Application No. WO93/16094. As is well known in the art, if the probe molecule and nucleic acid sample hybridize by forming a strong bond between the two molecules, it can be reasonably assumed that the probe and sample have substantial homology. Detection of the probe provides a means for determining in a known manner whether hybridization has occurred. Such a probe analysis provides a rapid method for identifying toxin-encoding genes of the subject invention.

The nucleotide segments which are used as probes according to the invention can be synthesized by use of DNA synthesizers using standard procedures. In the use of labeled nucleotide segments as probes, the particular probe is labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Preferably, hybridization is conducted under stringent conditions by techniques well known in the art, as described, for example, in Keller, G. H., M. M. Manak (1989) *DNA Probes,* Stockton Press, New York, N.Y., pp. 169–170. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid; a certain degree of mismatch can be tolerated. Therefore, the probes of the subject invention include mutations (both single and multiple), deletions, insertions of the described sequences, and combinations thereof wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

Specific nucleotide probes useful according to the subject invention in the rapid identification of CryIF class toxin genes include:

(i) DNA coding for a peptide sequence "Ser Thr Gly Arg Leu Pro Leu Asp" (SEQ ID NO. 9). A specific example of such a probe is "AGTACWGGMA GRTTACCRTT RGAY" (SEQ ID NO. 10);

(ii) DNA coding for a peptide sequence "Glu Asp Ser Pro Val Ser Ala Asn" (SEQ ID NO. 11). A specific example of such a probe is "GARGATTCWC CAGTWTCWGC WAAT" (SEQ ID NO. 12);

(iii) DNA coding for a peptide sequence "Asn Gly Phe Asn Arg Ala Glu Phe Gly Val" (SEQ ID NO. 13). A specific example of such a probe is "AATGGWTTTA ATAGTGCT-GAATTTGGGAGTW" (SEQ ID NO. 14);

(iv) DNA coding for a peptide sequence "Val Thr Ala Glu Thr Val Arg Ser Gln Thr" (SEQ ID NO. 15). A specific example of such a probe is "GTAACWGCAG ARACWGT-WAG WAGTCAAACW" (SEQ ID NO. 16);

(v) DNA coding for a peptide sequence "Val Phe Asn Pro Gly Gly Ala Ile Trp Ile Ala Asp Glu" (SEQ ID NO. 17). A specific example of such a probe is "GTMTTYAATC CWG-GWGGMGCMATWTGGATWGCWGATGARG AT" (SEQ ID NO. 18);

(vi) DNA coding for a peptide sequence "Val Arg Gly Gly Phe Gly" (SEQ ID NO. 19). A specific example of such a probe is "GTMMGAGGWG GWTTTGGR" (SEQ ID NO. 20);

(vii) DNA coding for a peptide sequence "Gly Thr Asn His Thr Arg Thr" (SEQ ID NO. 21). A specific example of such a probe is "GGWACRAAYC AYACMMGAAC W" (SEQ ID NO. 22);

(viii) DNA coding for a peptide sequence "Val Arg Trp Pro Gly Glu Ile" (SEQ ID NO. 23). A specific example of such a probe is "GTWMGATGGC CWGGWGARAT W" (SEQ ID NO. 24);

(ix) DNA coding for a peptide sequence "Ser Asp Ser Trp Arg Ala" (SEQ ID NO. 25). A specific example of such a probe is "AGTGATTCWT GGAGAGCW" (SEQ ID NO. 26).

Because of the redundancy of the genetic code, i.e., more than one coding nucleotide triplet (codon) can be used for most of the amino acids used to make proteins, different nucleotide sequences can code for a particular amino acid. Thus, the amino acid sequences of the *B.t.* toxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art.

Recombinant hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, live microbes can be applied to the situs of lepidopterans where they will proliferate and be ingested by the pest. The result is a control of this pest. Alternatively, the microbe hosting the toxin gene can be treated under conditions that prolong the activity of the toxin and stabilize the cell. The treated cell, which retains the toxic activity, then can be applied to the environment of the target pest.

Where the *B.t.* toxin gene is introduced via a suitable vector into a microbial host, and said host is applied to the environment in a living state, it is essential that certain host microbes be used. For example, microorganism hosts can be selected which are known to occupy the soil. These microorganisms are selected so as to be capable of successfully competing in the soil with the wild-type microorganisms. It is also important that they provide for stable maintenance and expression of the gene expressing the polypeptide pesticide, and, desirably, provide for improved protection of the pesticide from environmental degradation and inactivation.

A large number of microorganisms are known to inhabit the rhizosphere (the soil surrounding plant roots). These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes and Clostridium; fungi, particularly yeast, e.g., genera Saccharomyces, Cryptococcus, Kluyveromyces, Sporobolomyces, Rhodotorula, and Aureobasidium; microalgae, e.g., families Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae, and Chlorophyceae. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomycesroseus, S. odorus, Kluyveromycesveronae,* and *Aureobasidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., *Animal Tissue Techniques,* W. H. Freeman and Company, 1967); or a combination of physical (heat) and chemical agents that preserve and prolong the activity of the toxin produced in the cell when the cell is administered to the host's environment. In one preferred embodiment, acids can be used to stabilize the cells. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain a substantial portion of the bio-availability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the B.t. isolates, or recombinant microbes comprising the gene(s) obtainable from the B.t. isolates disclosed herein, can be applied to the soil. Formulated product can also be applied as a seed-coating or root treatment or total plant treatment at later stages of the crop cycle.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran, e.g., soil, by spraying, dusting, sprinkling, or the like.

Mutants. Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (–). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing of the B.t. Isolates of the Invention

A subculture of a novel B.t. isolate, or mutants thereof, can be used to inoculate the following medium, a peptone, glucose, salts medium.

| Bacto Peptone | 7.5 g/l |
|---|---|
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |

Salts Solution (100 ml)

| $MgSO_4 \cdot 7H_2O$ | 2.46 g |
|---|---|
| $MnSO_4 \cdot H_2O$ | 0.04 g |
| $ZnSO_4 \cdot 7H_2O$ | 0.28 g |
| $FeSO_4 \cdot 7H_2O$ | 0.40 g |

$CaCl_2$ Solution (100 ml)

| $CaCl_2 \cdot 2H_2O$ | 3.66 g |
|---|---|
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Activity of B.t. Isolates Against Lepidopterans

The following strains have been tested for anti-lepidopteran activity with the following results:

TABLE 6

| Bioassay results | | |
|---|---|---|
| | % Mortality | |
| Strain | *Trichoplusia ni* | *Spodoptera exigua* |
| PS81T1 | 96,8 | |
| PS53C2 | 100, 100 | |
| PS31F4 | | 100, 100 |
| PS86V1 | 100 | |
| PS86I2 | 100, 92 | |
| PS73E | 100, 100 | |
| PS81K | 100, 100 | |
| PS83E2 | 100, 100 | |
| PS81E | 100, 92 | |
| PS81Z3 | 100 | |
| PS53B5 | | 100 |
| PS83R | 100 | |
| PS53B2 | | 100 |
| PS83N2 | 100 | |
| PS81B5 | 100, 100 | |
| PS86W1 | 100 | |
| PS91C2 | 100, 100 | |
| PS81A2 | 100, 100 | |

*Spodoptera exigua* bioassay procedure. *B.t.* cultures were harvested and resuspended in sterile deionized water. Fixed volumes of each culture were incorporated into USDA Insect Diet (Technical Bulletin 1528, U.S. Department of Agriculture, 1976). Twenty-four neonate *S. exigua* were exposed to the diet for 6 days. Mortality readings were taken at this time.

*Trichoplusia ni* bioassay procedure. *B.t.* cultures were harvested and resuspended in sterile deionized water. Fixed volumes of each culture were top loaded onto USDA Insect Diet. Trays were infested with neonate *T. ni.* After 6 days mortality was determined.

EXAMPLE 3

Characterization of Toxin Genes by RFLP Analysis

Total cellular DNA was prepared from *Bacillus thuringiensis* (*B.t.*) cells grown to an optical density, at 600 mn, of 1.0. The cells were recovered by centrifugation, and protoplasts were prepared in TES buffer (30 mM Tris-HCl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform(1:1). The DNA was precipitated with ethanol and purified by isopycnic banding on a cesium chloride-ethidium bromide gradient.

Total cellular DNA isolated from *B.t.* cells was digested with a restriction endonuclease and separated by electrophoresison a 0.8% (w/v) agarose-TAE (50 mM Tris-HCl, 20 mM NaOAc, 2.5 mM EDTA, pH=8.0) buffered gel. A Southern blot of the gel was hybridized with the [$^{32}$P]-radiolabeled oligonucleotide probe, ATGATTCATGCGGCAGATA (SEQ ID NO. 5), and then washed to remove unbound radioactivity. The blot was exposed to KODAK X-OMAT™ film using standard autoradiography techniques. The results are an array of hybridizing bands (fingerprint) which correspond to toxin genes or toxin gene fragments. This type of characterization is known as Restriction Fragment Length Polymorphism (RFLP) analysis which classifies each isolate by a distinct DNA fingerprint.

TABLE 7

| DNA fingerprints for *B.t.* isolates of the subject invention | |
|---|---|
| Isolate | Hybridizing *Hind*III Fragments (Kb) |
| PS81T1 | 1.13, 3.0, 9.4 |
| PS53C2 | 1.052, 5.8, 6.6 |
| PS31F4 | 5.5, 8.0 |
| PS86V1 | 5.5, 6.0, 6.6 |
| PS86I2 | 5.0, 6.6, 7.5, 12 |
| PS73E | 1.052, 1.13, 3.0, 8.5 |
| PS81K | 3.2, 7.5, 9.4, 13 |
| PS83E2 | 3.2, 8.5, 12 |
| PS81E | 1.13, 3.2, 9.4 |
| PS81Z3 | 1.13, 3.0, 8.5 |
| PS53B5 | 1.13, 3.0, 7.5 |
| PS83R | 1.13, 3.0, 8.5, 12 |
| PS53B2 | 1.052, 1.13, 3.0, 7.5 |
| PS83N2 | 5.5 |
| PS81B5 | 8.0, 13 |
| PS86W1 | 5.5, 6.6 |
| PS91C2 | 1.13, 3.0, 6.0, 7.5, 8.5 |
| PS81A2 | 13, 16 |

TABLE 8

| Hybridizing *Hind*III fragments of *B.t.* isolates of the subject invention | |
|---|---|
| Isolate | Novel Hybridizing *Hind*III Fragments (~Kb) |
| PS91C2 | 3.0, 6.0, 7.5 |
| PS83E2 | 3.2 |
| PS86I2 | 5.0 |
| PS31F4 | 5.5, 8.0 |
| PS53C2 | 5.8 |
| PS81T1 | 9.4 |

EXAMPLE 4

Molecular Cloning and Expression of a Novel CryIF Toxin Gene from *Bacillus thuringiensis* Strain PS91C2

Total cellular DNA was prepared from *Bacillus thuringiensis* (*B.t.*) cells grown to an optical density, at 600 nm, of 1.0. Cells were pelleted by centrifugation and resuspended in protoplast buffer (20 mg/ml lysozyme in 0.3 M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 $\mu$g/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE buffer.

A 1.58 kbp fragment of the novel 130 kDa toxin gene was obtained by polymerase chain reaction (PCR) amplification-from PS91C2 cellular DNA using the following primers: forward 5'-GAGTGGGAAGCAGATCTTAATAATGCACAATTAAGG-3' (SEQ ID NO. 6) and reverse 5'-ATAC(C or T)CGATCGATATGATA(G or A)TCCGT-3' (SEQ ID NO.

7). This DNA fragment was cloned into pBluescript S/K (Stratagene, La Jolla, Calif.) and the DNA sequence determined by dideoxynucleotide sequencing methodology (Sanger et al. [1977] *Proc. Natl. Acad. Sci USA* 74:5463–5467) using Sequenase (U.S. Biochemicals, Cleveland, Ohio). DNA sequences unique to the CryIF gene were identified by computer comparison with other CryI genes. An oligonucleotide probe with the following sequence was synthesized: 5'-CCCAATGTGAATGTACTTTGCGC-3' (SEQ ID NO. 8). This probe was radiolabeled with $^{32}P$ and used in standard hybridizations of Southern blots of PS91 C2 total cellular DNA. Hybridizing bands included an approximately 7.5 kbp HindIII fragment.

A gene library was constructed from PS91C2 DNA partially digested with NdeII. Partial restriction digests were fractionated by agarose gel electrophoresis. DNA fragments 9.3 to 23 kbp in size were excised from the gel, electroeluted from the gel slice, purified on an Elutip D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coli* KW251 cells. Plaques were screened by hybridization with each of the respective probes described above. Hybridizing phage were plaque-purified and used to infect liquid cultures of *E. coli* KW251 cells for isolation of DNA by standard procedures (Maniatis et al., supra).

For subcloning the gene encoding the 130 kDa CryIF toxin, preparative amounts of phage DNA were digested with Sau3A and electrophoresed on agarose gel. The approximately 8 kbp band containing the toxin gene was excised from the gel, electroeluted from the gel slice, and purified by ion exchange chromatography as described above. The purified DNA insert was ligated into an XhoI-digested pHTBlueII (an *E. coli/B. thuringiensis* shuttle vector comprised of pBluescript S/K (Stratagene) and the replication origin from a resident *B.t.* plasmid (D. Lereclus et al. [1989] *FEMS Microbiol. Lett.* 60:211–218). The ligation mix was used to transform frozen, competent *E. coli* NM522 cells (ATCC 47000). β-galactosidase transformants were screened by restriction digestion of alkaline lysate plasmid minipreps as above. The desired plasmid construct, pMYC2361, contains a toxin gene that is novel compared to other toxin genes containing insecticidal proteins.

pMYC2361 was introduced into the acrystalliferous ($Cry^-$) *B.t.* host, CryB (A. Aronson, Purdue University, West Lafayette, Ind.) by electroporation. Expression of the 130 kDa toxin was demonstrated by SDS-PAGE analysis. NaBr-purified crystals were prepared (Pfannenstiel, M. A. et al. [1984] *FEMS Microbiol. Lett.* 21:39) for determination of toxicity of the cloned gene product to *Plutella xylostella* by the screening method described in Example 3. The $LC_{50}$ for the CryIF toxin against *P. xylostella* was determined to be 5 μg toxin/ml diet.

EXAMPLE 5

Insertion of Toxin Genes Into Plants

One aspect of the subject invention is the transformation of plants with genes encoding a lepidopteran toxin. The transformed plants are resistant to attack by lepidopterans.

Genes encoding lepidopteran-active toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 0 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsterset al. [1978] Mol. Gen. Genet. 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 6

Cloning of Novel *B.t.* Genes Into Insect Viruses

A number of viruses are known to infect insects. These viruses include, for example, baculoviruses and entomopoxviruses. In one embodiment of the subject invention, lepidopteran-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition of matter comprising *Bacillus thuringiensis* PS91C2, or a mutant thereof, or spores or crystals of said isolate, in association with an insecticide carrier.

2. A substantially pure toxin protein wherein said toxin has activity against a lepidopteran pest, and wherein said toxin comprises all or a lepidopteran-active part of SEQ ID NO. 4.

3. The toxin of claim 2 wherein said toxin has the amino acid sequence shown in SEQ ID NO. 4.

4. A toxin, free from naturally associated impurities, encoded by a nucleotide sequence obtainable from *Bacillus thuringiensis* PS91C2, or a portion of said nucleotide sequence, wherein said toxin is active against lepidopteran pests.

5. A toxin active against lepidopteran pests, wherein said toxin is free from naturally associated impurities, and wherein said toxin comprises an amino acid sequence shown in SEQ ID NO. 4 or a lepidopteran-active portion thereof.

* * * * *

UNITED STATES PATENT AND TRADEMARK OFFICE
CERTIFICATE OF CORRECTION

PATENT NO. : 5,985,267

DATED : November 16, 1999

INVENTOR(S) : Payne *et al.*

It is certified that error appears in the above-identified patent and that said Letters Patent is hereby corrected as shown below:

Column 2, line 12: "coleopteranpests" should read --coleopteran pests--.

Column 11, line 51: "Sporobolomycesroseus" should read --Sporobolomyces roseus--.

Column 11, line 52: "Kluyveromycesveronae" should read --Kluyveromyces veronae--.

Column 15, line 42: "600 mn." should read --600 nm.--.

Column 15, line 55 & 56: "electrophoresison" should read --electrophoresis on--.

Column 17, line 12: "PS91 C2" should read --PS91C2--.

Signed and Sealed this

Third Day of April, 2001

*Attest:*

NICHOLAS P. GODICI

*Attesting Officer* *Acting Director of the United States Patent and Trademark Office*

SEQUENCE LISTING

```
(1) GENERAL INFORMATION:

   (iii) NUMBER OF SEQUENCES: 27


(2) INFORMATION FOR SEQ ID NO:1:

     (i) SEQUENCE CHARACTERISTICS:
          (A) LENGTH: 3522 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Bacillus thuringiensis
          (B) STRAIN: aizawai
          (C) INDIVIDUAL ISOLATE: PS81A2

   (vii) IMMEDIATE SOURCE:
          (A) LIBRARY: Lambdagem - 11 (tm) Library of August Sick
          (B) CLONE: 81A2

    (xi) SEQUENCE DESCRIPTION: SEQ ID NO:1:

ATGGAGAATA ATATTGAAAA TCAATGCATA CCTTACAATT GTTTAAATAA TCCTGAAGTA      60

GAGATATTAG GGATTGAAAG GTCAAATAGT AACGTAGCAG CAGAAATCGG CTTGGGGCTT     120

AGTCGTCTGC TCGTTTCCCG AATTCCACTA GGGGATTTTA TACTTGGCTT GTTTGATGTA     180

ATATGGGGGG CTATAGGTCC TTCACAATGG GATATATTTT TAGAGCAAAT TGAGCTATTG     240

ATCGGCCAAA GAATAGAGGA ATTCGCTAGG AATCAGGCAA TTTCTAGATT ACAAGGGCTA     300

AGCAATCTTT ACCGAATTTA CACAAATGCT TTTAAAAACT GGGAAGTAGA TCCTACTAAT     360

CCAGCATTAA GAGAAGAGAT GCGTATTCAA TTTAATGACA TGAACAGTGC TCTTACAACA     420

GCTATTCCTC TTTTTTCAGT TCAAGGTTAT GAAATTCCTC TTTTATCAGT ATATGTTCAA     480

GCTGCAAATT TACATTTATC GGTTTTGAGA GATGTTTCAG TGTTTGGACA ACGTTGGGGA     540

TTTGATGTAG CAACAATCAA TAGTCGTTAT AATGATTTAA CTAGGCTTAT TGGCGAATAT     600
```

-continued

```
ACTGATTATG CTGTACGTTG GTATAATACG GGGTTAAATC GTTTACCACG TAATGAAGGG    660
GTACGAGGAT GGGCAAGATT TAATAGGTTT AGAAGAGAGT TAACAATATC AGTATTAGAT    720
ATTATTTCTT TTTTCCAAAA TTACGATTCT AGATTATATC CAATTCCGAC AATCTATCAA    780
TTAACGCGGG AAGTATATAC AGATCCGGTA ATTAATATAA CTGATTATAG AGTTACCCCA    840
AGTTTCGAGA GTATTGAAAA TTCAGCTATT AGAAGTCCCC ATCTTATGGA TTTCTTAAAT    900
AATATAATTA TTGACACTGA TTTAATTAGA GGCGTTCACT ATTGGGCGGG GCATCGTGTA    960
ACTTCTCATT TTACCGGTAG TTCGCAAGTG ATAAGCTCCC CTCAATACGG GATAACTGCA   1020
AACGCAGAAC CGAGTCGAAC TATTGCTCCT AGCACTTTTC CAGGTCTTAA TCTATTTTAT   1080
AGAACACTAT CAGACCCTTT CTTCCGAAGA TCCGATAATA TTATGCCAAC ATTAGGAATA   1140
AATGTAGTGC AGGGGGTAGG ATTCATTCAA CCAAATAATG GTGAAGTTCT ATATAGAAGG   1200
AGAGGAACAG TAGATTCTCT TGATGAGTTG CCAATTGACG GTGAGAATTC ATTAGTTGGA   1260
TATAGTCATA GATTAAGTCA CGTTACATTA ACCAGGTCGT TATATAATAC TAATATAACT   1320
AGCTTGCCAA CATTTGTTTG GACACATCAC AGTGCTACTG ATCGAAATAT AATCTATCCG   1380
GATGTAATTA CACAAATACC ATTGGTAAAA TCATTCTCCC TTACTTCAGG TACCTCTGTA   1440
GTCAGAGGCC CAGGATTTAC AGGAGGGGAT ATCATCCGAA CTAACGTTAA TGGTAATGTA   1500
CTAAGTATGA GTCTTAATTT TAGTAATACA TCATTACAGC GGTATCGCGT GAGAGTTCGT   1560
TATGCTGCTT CTCAAACAAT GGTCATGAGA GTAAATGTTG GAGGGAGTAC TACTTTTGAT   1620
CAAGGATTCC CTAGTACTAT GAGTGCAAAT GGGTCTTTGA CATCTCAATC ATTTAGATTT   1680
GCAGAATTTC CTGTAGGCAT TAGTACATCT GGCAGTCAAA CTGCTGGAAT AAGTATAAGT   1740
AATAATCCAG GTAGACAAAC GTTTCACTTA GATAGAATTG AATTTATCCC AGTTGATGCA   1800
ACATTTGAAG CAGAATATGA TTTAGAAAGA GCACAAAAGG CGGTGAATTC GCTGTTTACT   1860
TCTTCCAATC AAATCGAGTT AAAAACAGAT GTGACGGATT ATCATATTGA TCAAGTATCC   1920
AATTTAGTAG ATTGTTTATC CGATGAATTT TGTCTGGATG AAAAGCGAGA ATTGTCCGAG   1980
AAAGTCAAAC ATGCGAAGCG ACTCAGTGAT GAGCGGAATT TACTTCAAGA TCCAAACTTC   2040
AGAGGGATCA ATAGGCAACC AGACCGTGGC TGGAGAGGAA GTACGGATAT TACCATCCAA   2100
GGAGGAGATG ACGTATTCAA AGAGAATTAC GTCACACTAC CAGGTACCTT TGATGAGTGC   2160
TATCCAACGT ATTTGTATCA AAAAATAGAT GAGTCGAAAT TAAAAGCCTA TAACCGTTAC   2220
CAATTAAGAG GGTATATCGA AGATAGTCAA GACTTAGAAA TCTATTTAAT TCGCTACAAT   2280
GCAAAACACG AAACAGTAAA TGTACCAGGT ACGGGTTCCT TATGGCCGCT TTCAGTCGAA   2340
AGTCCAATTG GAAGGTGTGG AGAACCGAAT CGGTGTGTGC CACACCTTGA ATGGAATCCT   2400
GATTTAGATT GTTCCTGCAG AGACGGGGAA AAATGTGCAC ATCATTCCCA TCATTTCTCC   2460
TTGGACATTG ATGTTGGATG CACAGACTTG CAAGAGGATC TAGGCGTGTG GGTTGTATTC   2520
AAGATTAAGA CGCAGGAAGG TTATGCAAGA TTAGGAAATC TGGAATTTAT CGAAGAGAAA   2580
CCATTAATTG GAGAAGCACT GTCTCGTGTG AAGAGAGCGG AAAAAAAATG GAGAGACAAA   2640
CGGGAAAAAC TACAATTGGA AACAAAACGA GTATATACAG AGGCAAAAGA AGCTGTGGAT   2700
GCTTTATTCG TAGATTCTCA ATATGATAGA TTACAAGCAG ATACAAACAT TGGTATGATT   2760
CATGCGGCAG ATAGACTTGT TCATCAGATC CACGAGGCTT ATCTTCCAGA ACTACCTTTC   2820
ATTCCAGGAA TAAATGTGGT GATTTTTGAA GAATTAGAAA ACCGTATTTC TACTGCATTA   2880
TCCCTATATG ATGCGAGAAA TGTCATTAAA AATGGCGATT TCAATAATGG CTTATCATGC   2940
TGGAACGTGA AAGGGCATGT AGATGTAGTA GAACAAAACA ACCACCGTTC GGTCCTTGTT   3000
```

-continued

```
GTCCCGGAAT GGGAAGCAGA AGTGTCACAA ACAATTCGTG TCTGTCCGGG GCGTGGCTAT   3060

ATCCTCCGTG TTACAGCGTA CAAAGAGGGA TATGGAGAAG GTTGCGTAAC CATCCATGAG   3120

ATCGAGAACA ATACAGACGA ACTAAAATTT AAAAACTGTG AAGAAGAGGA AGTGTATCCA   3180

ACGGATACAG GAACGTGTAA TGATTATACT GCACACCAAG GTACAGCAGG ATCCACAGAT   3240

TCATGTAATT CCCGTAATAT CAGATATGAG GATGCATATG AAATGAATAC TACAGCATCT   3300

GTTAATTACA AACCGACTTA CGAAGAAGAA AGGTATACAG ATGTACAAGG AGATAATCAT   3360

TGTGAATATG ACAGAGGGTA TGTGAATTAT CGACCAGTAC CAGCTGGTTA TGTGACAAAA   3420

GAATTAGAGT ACTTCCCAGA AACCGATAAG GTATGGATTG AGATCGGAGA AACGGAAGGG   3480

AAGTTTATTG TAGACAATGT CGAATTACTC CTTATGGAGG AA                      3522
```

(2) INFORMATION FOR SEQ ID NO:2:

(i) SEQUENCE CHARACTERISTICS:
(A) LENGTH: 1174 amino acids
(B) TYPE: amino acid
(C) STRANDEDNESS: single
(D) TOPOLOGY: linear (ii) MOLECULE TYPE: protein (iii) HYPOTHETICAL: YES (iv) ANTI-SENSE: NO (vi) ORIGINAL SOURCE:
(A) ORGANISM: Bacillus thuringiensis
(B) STRAIN: aizawai
(C) INDIVIDUAL ISOLATE: PS81A2

(vii) IMMEDIATE SOURCE:
(A) LIBRARY: Lambdagem - 11 (tm) Library of August Sick
(B) CLONE: 81A2

(xi) SEQUENCE DESCRIPTION: SEQ ID NO:2:

```
Met Glu Asn Asn Ile Glu Asn Gln Cys Ile Pro Tyr Asn Cys Leu Asn
1               5                   10                  15

Asn Pro Glu Val Glu Ile Leu Gly Ile Glu Arg Ser Asn Ser Asn Val
            20                  25                  30

Ala Ala Glu Ile Gly Leu Gly Leu Ser Arg Leu Leu Val Ser Arg Ile
        35                  40                  45

Pro Leu Gly Asp Phe Ile Leu Gly Leu Phe Asp Val Ile Trp Gly Ala
    50                  55                  60

Ile Gly Pro Ser Gln Trp Asp Ile Phe Leu Glu Gln Ile Glu Leu Leu
65                  70                  75                  80

Ile Gly Gln Arg Ile Glu Glu Phe Ala Arg Asn Gln Ala Ile Ser Arg
                85                  90                  95

Leu Gln Gly Leu Ser Asn Leu Tyr Arg Ile Tyr Thr Asn Ala Phe Lys
            100                 105                 110

Asn Trp Glu Val Asp Pro Thr Asn Pro Ala Leu Arg Glu Glu Met Arg
        115                 120                 125

Ile Gln Phe Asn Asp Met Asn Ser Ala Leu Thr Thr Ala Ile Pro Leu
    130                 135                 140

Phe Ser Val Gln Gly Tyr Glu Ile Pro Leu Leu Ser Val Tyr Val Gln
145                 150                 155                 160

Ala Ala Asn Leu His Leu Ser Val Leu Arg Asp Val Ser Val Phe Gly
                165                 170                 175

Gln Arg Trp Gly Phe Asp Val Ala Thr Ile Asn Ser Arg Tyr Asn Asp
            180                 185                 190
```

-continued

```
Leu Thr Arg Leu Ile Gly Glu Tyr Thr Asp Tyr Ala Val Arg Trp Tyr
        195                 200                 205

Asn Thr Gly Leu Asn Arg Leu Pro Arg Asn Glu Gly Val Arg Gly Trp
    210                 215                 220

Ala Arg Phe Asn Arg Phe Arg Arg Glu Leu Thr Ile Ser Val Leu Asp
225                 230                 235                 240

Ile Ile Ser Phe Phe Gln Asn Tyr Asp Ser Arg Leu Tyr Pro Ile Pro
                245                 250                 255

Thr Ile Tyr Gln Leu Thr Arg Glu Val Tyr Thr Asp Pro Val Ile Asn
            260                 265                 270

Ile Thr Asp Tyr Arg Val Thr Pro Ser Phe Glu Ser Ile Glu Asn Ser
        275                 280                 285

Ala Ile Arg Ser Pro His Leu Met Asp Phe Leu Asn Asn Ile Ile Ile
    290                 295                 300

Asp Thr Asp Leu Ile Arg Gly Val His Tyr Trp Ala Gly His Arg Val
305                 310                 315                 320

Thr Ser His Phe Thr Gly Ser Ser Gln Val Ile Ser Ser Pro Gln Tyr
                325                 330                 335

Gly Ile Thr Ala Asn Ala Glu Pro Ser Arg Thr Ile Ala Pro Ser Thr
            340                 345                 350

Phe Pro Gly Leu Asn Leu Phe Tyr Arg Thr Leu Ser Asp Pro Phe Phe
        355                 360                 365

Arg Arg Ser Asp Asn Ile Met Pro Thr Leu Gly Ile Asn Val Val Gln
    370                 375                 380

Gly Val Gly Phe Ile Gln Pro Asn Asn Gly Glu Val Leu Tyr Arg Arg
385                 390                 395                 400

Arg Gly Thr Val Asp Ser Leu Asp Glu Leu Pro Ile Asp Gly Glu Asn
                405                 410                 415

Ser Leu Val Gly Tyr Ser His Arg Leu Ser His Val Thr Leu Thr Arg
            420                 425                 430

Ser Leu Tyr Asn Thr Asn Ile Thr Ser Leu Pro Thr Phe Val Trp Thr
        435                 440                 445

His His Ser Ala Thr Asp Arg Asn Ile Ile Tyr Pro Asp Val Ile Thr
    450                 455                 460

Gln Ile Pro Leu Val Lys Ser Phe Ser Leu Thr Ser Gly Thr Ser Val
465                 470                 475                 480

Val Arg Gly Pro Gly Phe Thr Gly Gly Asp Ile Ile Arg Thr Asn Val
                485                 490                 495

Asn Gly Asn Val Leu Ser Met Ser Leu Asn Phe Ser Asn Thr Ser Leu
            500                 505                 510

Gln Arg Tyr Arg Val Arg Val Arg Tyr Ala Ala Ser Gln Thr Met Val
        515                 520                 525

Met Arg Val Asn Val Gly Gly Ser Thr Thr Phe Asp Gln Gly Phe Pro
    530                 535                 540

Ser Thr Met Ser Ala Asn Gly Ser Leu Thr Ser Gln Ser Phe Arg Phe
545                 550                 555                 560

Ala Glu Phe Pro Val Gly Ile Ser Thr Ser Gly Ser Gln Thr Ala Gly
                565                 570                 575

Ile Ser Ile Ser Asn Asn Pro Gly Arg Gln Thr Phe His Leu Asp Arg
            580                 585                 590

Ile Glu Phe Ile Pro Val Asp Ala Thr Phe Glu Ala Glu Tyr Asp Leu
        595                 600                 605

Glu Arg Ala Gln Lys Ala Val Asn Ser Leu Phe Thr Ser Ser Asn Gln
    610                 615                 620
```

-continued

```
Ile Glu Leu Lys Thr Asp Val Thr Asp Tyr His Ile Asp Gln Val Ser
625                 630                 635                 640

Asn Leu Val Asp Cys Leu Ser Asp Glu Phe Cys Leu Asp Glu Lys Arg
                645                 650                 655

Glu Leu Ser Glu Lys Val Lys His Ala Lys Arg Leu Ser Asp Glu Arg
            660                 665                 670

Asn Leu Leu Gln Asp Pro Asn Phe Arg Gly Ile Asn Arg Gln Pro Asp
        675                 680                 685

Arg Gly Trp Arg Gly Ser Thr Asp Ile Thr Ile Gln Gly Gly Asp Asp
    690                 695                 700

Val Phe Lys Glu Asn Tyr Val Thr Leu Pro Gly Thr Phe Asp Glu Cys
705                 710                 715                 720

Tyr Pro Thr Tyr Leu Tyr Gln Lys Ile Asp Glu Ser Lys Leu Lys Ala
                725                 730                 735

Tyr Asn Arg Tyr Gln Leu Arg Gly Tyr Ile Glu Asp Ser Gln Asp Leu
            740                 745                 750

Glu Ile Tyr Leu Ile Arg Tyr Asn Ala Lys His Glu Thr Val Asn Val
        755                 760                 765

Pro Gly Thr Gly Ser Leu Trp Pro Leu Ser Val Glu Ser Pro Ile Gly
    770                 775                 780

Arg Cys Gly Glu Pro Asn Arg Cys Val Pro His Leu Glu Trp Asn Pro
785                 790                 795                 800

Asp Leu Asp Cys Ser Cys Arg Asp Gly Glu Lys Cys Ala His His Ser
                805                 810                 815

His His Phe Ser Leu Asp Ile Asp Val Gly Cys Thr Asp Leu Gln Glu
            820                 825                 830

Asp Leu Gly Val Trp Val Val Phe Lys Ile Lys Thr Gln Glu Gly Tyr
        835                 840                 845

Ala Arg Leu Gly Asn Leu Glu Phe Ile Glu Glu Lys Pro Leu Ile Gly
    850                 855                 860

Glu Ala Leu Ser Arg Val Lys Arg Ala Glu Lys Lys Trp Arg Asp Lys
865                 870                 875                 880

Arg Glu Lys Leu Gln Leu Glu Thr Lys Arg Val Tyr Thr Glu Ala Lys
                885                 890                 895

Glu Ala Val Asp Ala Leu Phe Val Asp Ser Gln Tyr Asp Arg Leu Gln
            900                 905                 910

Ala Asp Thr Asn Ile Gly Met Ile His Ala Ala Asp Arg Leu Val His
        915                 920                 925

Gln Ile His Glu Ala Tyr Leu Pro Glu Leu Pro Phe Ile Pro Gly Ile
    930                 935                 940

Asn Val Val Ile Phe Glu Glu Leu Glu Asn Arg Ile Ser Thr Ala Leu
945                 950                 955                 960

Ser Leu Tyr Asp Ala Arg Asn Val Ile Lys Asn Gly Asp Phe Asn Asn
                965                 970                 975

Gly Leu Ser Cys Trp Asn Val Lys Gly His Val Asp Val Val Glu Gln
            980                 985                 990

Asn Asn His Arg Ser Val Leu Val Val Pro Glu Trp Glu Ala Glu Val
        995                 1000                1005

Ser Gln Thr Ile Arg Val Cys Pro Gly Arg Gly Tyr Ile Leu Arg Val
    1010                1015                1020

Thr Ala Tyr Lys Glu Gly Tyr Gly Glu Gly Cys Val Thr Ile His Glu
1025                1030                1035                1040

Ile Glu Asn Asn Thr Asp Glu Leu Lys Phe Lys Asn Cys Glu Glu Glu
```

-continued

```
            1045                1050                1055

Glu Val Tyr Pro Thr Asp Thr Gly Thr Cys Asn Asp Tyr Thr Ala His
            1060                1065                1070

Gln Gly Thr Ala Gly Ser Thr Asp Ser Cys Asn Ser Arg Asn Ile Arg
        1075                1080                1085

Tyr Glu Asp Ala Tyr Glu Met Asn Thr Thr Ala Ser Val Asn Tyr Lys
    1090                1095                1100

Pro Thr Tyr Glu Glu Glu Arg Tyr Thr Asp Val Gln Gly Asp Asn His
1105                1110                1115                1120

Cys Glu Tyr Asp Arg Gly Tyr Val Asn Tyr Arg Pro Val Pro Ala Gly
                1125                1130                1135

Tyr Val Thr Lys Glu Leu Glu Tyr Phe Pro Glu Thr Asp Lys Val Trp
            1140                1145                1150

Ile Glu Ile Gly Glu Thr Glu Gly Lys Phe Ile Val Asp Asn Val Glu
        1155                1160                1165

Leu Leu Leu Met Glu Glu
    1170
```

(2) INFORMATION FOR SEQ ID NO:3:

(i) SEQUENCE CHARACTERISTICS:
(A) LENGTH: 3504 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bacillus thuringiensis
(B) STRAIN: Morrissoni
(C) INDIVIDUAL ISOLATE: PS91C2

(vii) IMMEDIATE SOURCE:
(A) LIBRARY: LambdaGem (TM) - 11 Library of Teresa Thompson
(B) CLONE: 91C2

(xi) SEQUENCE DESCRIPTION: SEQ ID NO:3:

```
ATGAAGAATA ACATTCAAAA TCAATGCGTA CCTTACAATT GTTTAAGTAA TCCTGAAGTA     60

GAAATATTAA GTGAAGAAAG AAGTACTGGC AGATTACCGT TAGATATATC CTTGTCGCTT    120

ACACGTTTCC TTTTGAGTGA ATTTGTTCCA GGTGTGGGAG TTGCGTTTGG ATTATTTGAT    180

TTAATATGGG GTTTTATAAC TCCTTCTGAA TGGAGTTTAT TTCTTTTACA GATTGAACAA    240

CTGATTGAAC AAAGAATTGA AACATTGGAA AGGAACCGGG CAATTACTAC ATTACGAGGG    300

TTAGCGGATA GCTATGAAGT TTACCTTGAG GCACTAAGAG AGTGGGAAGA AAATCCTAAT    360

AATGCACAAT TAAGGGAAGA TGTGCGTATT CGATTTGCTA ATACAGACGA CGCTTTAATA    420

ACAGCAATAA ATAATTTTAC ACTTACAAGT TTTGAAATCC CTCTTTTATC GGTCTATGTT    480

CAAGCGGCGA ATCTACATTT ATCACTATTA AGAGATGCTG TATCGTTTGG GCAGGGTTGG    540

GGGCTGGATA TAGCTACTGT TAATAATCAT TATAATAGAT TAATAAATCT TATTCATAGA    600

TATACGGAAC ATTGTTTGGA CACATACAAT CAAGGATTAG AAAACTTAAG AGGTACTAAT    660

ACTCGACAAT GGTCAAGATT CAATCAGTTT AGGAGAGAGT TAACATTGAC TGTATTAGAT    720

ATCGTTGCTC TTTTTCCGAA CTACGATGCT AGAGCATATC CAATTCAAAC GTCATCCCAA    780

TTAACAAGGG AAATTTATAC AAGTTCAGTA ATTGAAGATT CTCCAGTTTC TGCTAATATA    840
```

-continued

```
CCTAATGGTT TTAATAGAGC GGAATTTGGA GTTAGACCGC CCCATCTTAT GGACTTTATG    900
AATTCTTTGT TTGTAACTGC AGAGACTGTT AGAAGTCAAA CTGTGTGGGG AGGACACTTA    960
GTTAGTTCAC GAAATACGGC TGGTAACCCT ATAAATTTCC CTATTTATGG GGTCTTCAAT   1020
CCTGGTGGCG CCATTTGGAT TGCAGATGAG GATCCACGTC CTTTTTATCG GACATTATCA   1080
GATCCTGTTT TTGTCCGAGG AGGATTTGGG GATCCTCATT ATGTACTTGG GCTTAGGGGA   1140
GTAGGATTTC AACAAACTGG TACGAACCAC ACCCGAACAT TTAGAAATAG TGGGACCATA   1200
GATTCTCTAG ATGAAATCCC ACCTCAGGAT AATAGTGGGG CACCTTGGAA TGATTATAGT   1260
CATGTATTAA ATCATGTTAC ATTTGTAAGG TGGCCTGGTG AGATTGCAGG AAGTGATTCA   1320
TGGAGAGCGC CAATGTTTTC TTGGACACAC CGTAGTGCAG ATCGTACAAA TATCATTAAT   1380
CCAAATATAA TTACACAAAT ACCTGCTGTA AAAGCACACA ATCTTCATTC GGGTTCTACG   1440
GTTGTTAGAG GACCCGGGTT TACAGGTGGT GATCTCTTAC GAAGAACGAA TACTGGTACA   1500
TTTGCAGATA TAAGAGTAAA TATTACTGGG CCATTATCTC AAAGATATCG TGTAAGAATT   1560
CGCTATGCTT CTACGACAGA TTTACAATTT TTCACGAGAA TCAATGGAAC TTCTGTAAAT   1620
CAAGGTAATT TCCAAAGAAC TATGAATAGA GGGGATAATT TAGAATCTGG AAACTTTAGG   1680
ACTGCAGGAT TTAGTACGCC TTTTAGTTTT TCAAATGCGC AAAGTACATT CACATTGGGT   1740
ACTCAGGCTT TTTCAAATCA GGAAGTTTAT ATAGATCGAA TTGAATTTGT CCCGGCAGAA   1800
GTAACATTCG AGGCAGAATC TGATTTAGAA AGAGCGCAAA AGGCGGTGAA TGCCCTGTTT   1860
ACTTCTACAA GCCAACTAGG GCTAAAAACA AATGTAACGG GTTACCATAT TGATCAAGTG   1920
TCCAATTTAG TTGCGTGTTT ATCGGATGAA TTTTGTCTGG ATGAAAAGAG AGAATTGTCC   1980
GAGAAAGTTA AACATGCGAA GCGACTCAGT GATAAGCGGA ATTTACTTCA AGATCCAAAC   2040
TTCAGAGGGA TCAATAGGCA ACCAGACCAT GGCTGGAGAG GAAGTACGGA TATTACTATC   2100
CAAGGAGGAG ATGACGTATT CAAAGAGAAT TACGTTACGC TACCGGGTAC TTTTGATGAG   2160
TGCTATCCAA CGTATTTATA TCAAAAAATA GATGAGTCGA AATTAAAAGC CTATACCCGT   2220
TATCAATTAA GAGGGTATAT CGAAGATAGT CAAGACTTAG AAATCTATTT AATTCGTTAC   2280
AATTCAAAAC ACGAAATAGT AAATGTACCA GGTACAGGGA GTTTATGGCC TCTTTCTGTA   2340
GAAAATCAAA TTGGACCTTG TGGAGAACCG AATCGATGCG CGCCACACCT TGAATGGAAT   2400
CCTGATTTAC ACTGTTCCTG CAGAGACGGG GAAAAATGTG TGCATCATTC TCATCATTTC   2460
TCTTTGGACA TTGATGTCGG ATGTACAGAT TTAAATGAGG ACCTAGGTGT ATGGTTGATA   2520
TTCAAGATTA AGACGCAAGA TGGCCACGCA AGACTAGGGA ATCTAGAGTT TCTCGAAGAG   2580
GAACCGTTAT TAGGCGAAGC GTTAGGACGT GTGAAGAGAG CGGAGAAGAA GTGGAGAGAC   2640
AAACGCGAGA AACTGCAGTT GGAAACAAAT ATTGTCTATA AAGAGGCAAA AGAATCTGTA   2700
GATGCTTTAT TTGTAAACTC TCAATATGAT AGATTACAAG CGGATACGAA CATCGCGATG   2760
ATTCATGCGG CAGATAAACG CGTTCATAGA ATCCGGGAAG CGTATCTGCC AGAGTTGTCT   2820
GTGATTCCAG GTGTCAATGC GGCCATTTTC GAAGAATTAG AGGGACGTAT TTTTACAGCG   2880
TATTCCTTAT ATGATGCGAG AAATGTTATT AAAAATGGCA ATTTCAATAA TGGCTTATTA   2940
TGCTGGAACG TGAAAGGGCA TGTAGATGTA GAAGAGCAAA ACAACCACCG TTCGGTCCTT   3000
GTTGTTCCGG AATGGGAAGC AGAAGTGTCA CAAGAAGTTC GTGTCTGTCC GGGTCGTGGC   3060
TATATCCTTC GTGTCACAGC GTACAAAGAG GGATATGGAG AAGGCTGCGT AACTATTCAT   3120
GAAGTCGATA ATAATACAGA CGAATTGAAG TTTAGCAACT GTGAGAAAGA ACAAGTATAT   3180
CCAGGTAATA CGGTAGCATG TAATGATTAT AATAAGAATC ACGGTGCGAA TGCATGTAGT   3240
```

```
TCTCGTAATC GTGGATATGA CGAATCTTAT GAAAGTAATT CTTCCATACC AGCTGATTAT   3300

GCACCGGTTT ATGAAGAAGA AGCGTATACA GATGGACAAA GAGGGAATCC TTGTGAATTT   3360

AACAGAGGGC ATACACCATT ACCAGCTGGT TATGTGACAG CAGAGTTAGA GTACTTCCCA   3420

GAAACGGATA CAGTATGGGT TGAGATTGGA GAAACGGAAG GAACATTTAT CGTGGACAGT   3480

GTGGAATTAC TCCTTATGGA GGAA                                          3504
```

(2) INFORMATION FOR SEQ ID NO:4:

(i) SEQUENCE CHARACTERISTICS:
(A) LENGTH: 1168 amino acids
(B) TYPE: amino acid
(C) STRANDEDNESS: single
(D) TOPOLOGY: linear (ii) MOLECULE TYPE: protein (iii) HYPOTHETICAL: YES (iv) ANTI-SENSE: NO (vi) ORIGINAL SOURCE:
(A) ORGANISM: BACILLUS THURINGIENSIS
(B) STRAIN: Morrissoni
(C) INDIVIDUAL ISOLATE: PS91C2

(vii) IMMEDIATE SOURCE:
(A) LIBRARY: LAMBDAGEM (TM) - 11 LIBRARY OF TERESA THOMPSON
(B) CLONE: 91C2

(xi) SEQUENCE DESCRIPTION: SEQ ID NO:4:

```
Met Lys Asn Asn Ile Gln Asn Gln Cys Val Pro Tyr Asn Cys Leu Ser
1               5                   10                  15

Asn Pro Glu Val Glu Ile Leu Ser Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Glu Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Val Tyr Leu Glu Ala Leu
            100                 105                 110

Arg Glu Trp Glu Glu Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Glu His Cys Leu Asp Thr
        195                 200                 205

Tyr Asn Gln Gly Leu Glu Asn Leu Arg Gly Thr Asn Thr Arg Gln Trp
    210                 215                 220
```

-continued

```
Ser Arg Phe Asn Gln Phe Arg Arg Glu Leu Thr Leu Thr Val Leu Asp
225                 230                 235                 240

Ile Val Ala Leu Phe Pro Asn Tyr Asp Ala Arg Ala Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Pro Ile Asn Phe Pro Ile Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asp Pro His Tyr Val Leu Gly Leu Arg Gly Val Gly Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ala Gly Ser Asp Ser Trp Arg Ala Pro Met Phe Ser Trp
        435                 440                 445

Thr His Arg Ser Ala Asp Arg Thr Asn Ile Ile Asn Pro Asn Ile Ile
    450                 455                 460

Thr Gln Ile Pro Ala Val Lys Ala His Asn Leu His Ser Gly Ser Thr
465                 470                 475                 480

Val Val Arg Gly Pro Gly Phe Thr Gly Gly Asp Leu Leu Arg Arg Thr
                485                 490                 495

Asn Thr Gly Thr Phe Ala Asp Ile Arg Val Asn Ile Thr Gly Pro Leu
            500                 505                 510

Ser Gln Arg Tyr Arg Val Arg Ile Arg Tyr Ala Ser Thr Thr Asp Leu
        515                 520                 525

Gln Phe Phe Thr Arg Ile Asn Gly Thr Ser Val Asn Gln Gly Asn Phe
    530                 535                 540

Gln Arg Thr Met Asn Arg Gly Asp Asn Leu Glu Ser Gly Asn Phe Arg
545                 550                 555                 560

Thr Ala Gly Phe Ser Thr Pro Phe Ser Phe Ser Asn Ala Gln Ser Thr
                565                 570                 575

Phe Thr Leu Gly Thr Gln Ala Phe Ser Asn Gln Glu Val Tyr Ile Asp
            580                 585                 590

Arg Ile Glu Phe Val Pro Ala Glu Val Thr Phe Glu Ala Glu Ser Asp
        595                 600                 605

Leu Glu Arg Ala Gln Lys Ala Val Asn Ala Leu Phe Thr Ser Thr Ser
    610                 615                 620

Gln Leu Gly Leu Lys Thr Asn Val Thr Gly Tyr His Ile Asp Gln Val
625                 630                 635                 640

Ser Asn Leu Val Ala Cys Leu Ser Asp Glu Phe Cys Leu Asp Glu Lys
                645                 650                 655
```

-continued

```
Arg Glu Leu Ser Glu Lys Val Lys His Ala Lys Arg Leu Ser Asp Lys
            660                 665                 670

Arg Asn Leu Leu Gln Asp Pro Asn Phe Arg Gly Ile Asn Arg Gln Pro
        675                 680                 685

Asp His Gly Trp Arg Gly Ser Thr Asp Ile Thr Ile Gln Gly Gly Asp
    690                 695                 700

Asp Val Phe Lys Glu Asn Tyr Val Thr Leu Pro Gly Thr Phe Asp Glu
705                 710                 715                 720

Cys Tyr Pro Thr Tyr Leu Tyr Gln Lys Ile Asp Glu Ser Lys Leu Lys
                725                 730                 735

Ala Tyr Thr Arg Tyr Gln Leu Arg Gly Tyr Ile Glu Asp Ser Gln Asp
            740                 745                 750

Leu Glu Ile Tyr Leu Ile Arg Tyr Asn Ser Lys His Glu Ile Val Asn
        755                 760                 765

Val Pro Gly Thr Gly Ser Leu Trp Pro Leu Ser Val Glu Asn Gln Ile
    770                 775                 780

Gly Pro Cys Gly Glu Pro Asn Arg Cys Ala Pro His Leu Glu Trp Asn
785                 790                 795                 800

Pro Asp Leu His Cys Ser Cys Arg Asp Gly Glu Lys Cys Val His His
                805                 810                 815

Ser His His Phe Ser Leu Asp Ile Asp Val Gly Cys Thr Asp Leu Asn
            820                 825                 830

Glu Asp Leu Gly Val Trp Leu Ile Phe Lys Ile Lys Thr Gln Asp Gly
        835                 840                 845

His Ala Arg Leu Gly Asn Leu Glu Phe Leu Glu Glu Glu Pro Leu Leu
    850                 855                 860

Gly Glu Ala Leu Gly Arg Val Lys Arg Ala Glu Lys Lys Trp Arg Asp
865                 870                 875                 880

Lys Arg Glu Lys Leu Gln Leu Glu Thr Asn Ile Val Tyr Lys Glu Ala
                885                 890                 895

Lys Glu Ser Val Asp Ala Leu Phe Val Asn Ser Gln Tyr Asp Arg Leu
            900                 905                 910

Gln Ala Asp Thr Asn Ile Ala Met Ile His Ala Ala Asp Lys Arg Val
        915                 920                 925

His Arg Ile Arg Glu Ala Tyr Leu Pro Glu Leu Ser Val Ile Pro Gly
    930                 935                 940

Val Asn Ala Ala Ile Phe Glu Glu Leu Glu Gly Arg Ile Phe Thr Ala
945                 950                 955                 960

Tyr Ser Leu Tyr Asp Ala Arg Asn Val Ile Lys Asn Gly Asn Phe Asn
                965                 970                 975

Asn Gly Leu Leu Cys Trp Asn Val Lys Gly His Val Asp Val Glu Glu
            980                 985                 990

Gln Asn Asn His Arg Ser Val Leu Val Val Pro Glu Trp Glu Ala Glu
        995                 1000                1005

Val Ser Gln Glu Val Arg Val Cys Pro Gly Arg Gly Tyr Ile Leu Arg
    1010                1015                1020

Val Thr Ala Tyr Lys Glu Gly Tyr Gly Glu Gly Cys Val Thr Ile His
1025                1030                1035                1040

Glu Val Asp Asn Asn Thr Asp Glu Leu Lys Phe Ser Asn Cys Glu Lys
                1045                1050                1055

Glu Gln Val Tyr Pro Gly Asn Thr Val Ala Cys Asn Asp Tyr Asn Lys
            1060                1065                1070

Asn His Gly Ala Asn Ala Cys Ser Ser Arg Asn Arg Gly Tyr Asp Glu
```

-continued

```
        1075                1080                1085

Ser Tyr Glu Ser Asn Ser Ser Ile Pro Ala Asp Tyr Ala Pro Val Tyr
    1090                1095                1100

Glu Glu Glu Ala Tyr Thr Asp Gly Gln Arg Gly Asn Pro Cys Glu Phe
1105                1110                1115                1120

Asn Arg Gly His Thr Pro Leu Pro Ala Gly Tyr Val Thr Ala Glu Leu
                1125                1130                1135

Glu Tyr Phe Pro Glu Thr Asp Thr Val Trp Val Glu Ile Gly Glu Thr
            1140                1145                1150

Glu Gly Thr Phe Ile Val Asp Ser Val Glu Leu Leu Leu Met Glu Glu
        1155                1160                1165
```

(2) INFORMATION FOR SEQ ID NO:5:

(i) SEQUENCE CHARACTERISTICS:
(A) LENGTH: 19 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:5:

ATGATTCATG CGGCAGATA 19

(2) INFORMATION FOR SEQ ID NO:6:

(i) SEQUENCE CHARACTERISTICS:
(A) LENGTH: 36 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:6:

GAGTGGGAAG CAGATCTTAA TAATGCACAA TTAAGG 36

(2) INFORMATION FOR SEQ ID NO:7:

(i) SEQUENCE CHARACTERISTICS:
(A) LENGTH: 25 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:7:

ATACYCGATC GATATGATAR TCCGT 25

(2) INFORMATION FOR SEQ ID NO:8:

(i) SEQUENCE CHARACTERISTICS:
(A) LENGTH: 23 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:8:

CCCAATGTGA ATGTACTTTG CGC 23

(2) INFORMATION FOR SEQ ID NO:9:

-continued (i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

```
Ser Thr Gly Arg Leu Pro Leu Asp
                  5
```

(2) INFORMATION FOR SEQ ID NO:10:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:10:

AGTACWGGMA GRTTACCRTT RGAY 24

(2) INFORMATION FOR SEQ ID NO:11:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

```
Glu Asp Ser Pro Val Ser Ala Asn
                  5
```

(2) INFORMATION FOR SEQ ID NO:12:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:12:

GARGATTCWC CAGTWTCWGC WAAT 24

(2) INFORMATION FOR SEQ ID NO:13:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:13:

```
Asn Gly Phe Asn Arg Ala Glu Phe Gly Val
                  5                  10
```

(2) INFORMATION FOR SEQ ID NO:14:

(i) SEQUENCE CHARACTERISTICS:
(A) LENGTH: 31 bases (B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:14:

AATGGWTTTA ATAGTGCTGA ATTTGGGAGT W 31

(2) INFORMATION FOR SEQ ID NO:15:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:15:

```
Val Thr Ala Glu Thr Val Arg Ser Gln Thr
                5                   10
```

(2) INFORMATION FOR SEQ ID NO:16:

(i) SEQUENCE CHARACTERISTICS:
(A) LENGTH: 30 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:16:

GTAACWGCAG ARACWGTWAG WAGTCAAACW 30

(2) INFORMATION FOR SEQ ID NO:17:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

```
Val Phe Asn Pro Gly Gly Ala Ile Trp Ile Ala Asp Glu
                5                   10
```

(2) INFORMATION FOR SEQ ID NO:18:

(i) SEQUENCE CHARACTERISTICS:
(A) LENGTH: 42 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:18:

GTMTTYAATC CWGGWGGMGC MATWTGGATW GCWGATGARG AT 42

(2) INFORMATION FOR SEQ ID NO:19:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:19:

```
Val Arg Gly Gly Phe Gly
                 5
```

(2) INFORMATION FOR SEQ ID NO:20:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:20:

GTMMGAGGWG GWTTTGGR 18

(2) INFORMATION FOR SEQ ID NO:21:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:21:

```
Gly Thr Asn His Thr Arg Thr
                 5
```

(2) INFORMATION FOR SEQ ID NO:22:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:22:

GGWACRAAYC AYACMMGAAC W 21

(2) INFORMATION FOR SEQ ID NO:23:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:23:

```
Val Arg Trp Pro Gly Glu Ile
                 5
```

(2) INFORMATION FOR SEQ ID NO:24:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:24:

GTWMGATGGC CWGGWGARAT W 21

(2) INFORMATION FOR SEQ ID NO:25:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:25:

```
Ser Asp Ser Trp Arg Ala
                 5
```

(2) INFORMATION FOR SEQ ID NO:26:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:26:

AGTGATTCWT GGAGAGCW 18

(2) INFORMATION FOR SEQ ID NO:27:

(i) SEQUENCE CHARACTERISTICS:
(A) LENGTH: 1174 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:27:

```
Met Xaa Asn Asn Ile Gln Asn Gln Cys Val Pro Tyr Asn Cys Leu Xaa
1               5                   10                  15

Asn Pro Glu Val Glu Ile Leu Xaa Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Xaa Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Xaa Tyr Xaa Glu Ala Leu
            100                 105                 110

Arg Glu Trp Glu Xaa Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
```

-continued

```
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Xaa His Cys Leu Asp Thr
        195                 200                 205

Tyr Asn Gln Gly Leu Glu Asn Leu Arg Gly Thr Asn Thr Arg Gln Trp
    210                 215                 220

Xaa Arg Phe Asn Gln Phe Arg Arg Xaa Leu Thr Leu Thr Val Leu Asp
225                 230                 235                 240

Ile Val Ala Leu Phe Pro Asn Tyr Asp Xaa Arg Xaa Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Xaa Ile Asn Phe Pro Xaa Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Xaa Pro His Tyr Val Leu Gly Leu Arg Gly Val Xaa Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Xaa Gly Ser Asp Ser Trp Arg Ala Pro Met Phe Ser Trp
        435                 440                 445

Thr His Arg Ser Ala Xaa Xaa Thr Asn Xaa Ile Xaa Pro Xaa Xaa Ile
    450                 455                 460

Thr Gln Ile Pro Xaa Val Xaa Ala His Xaa Leu Xaa Ser Gly Xaa Thr
465                 470                 475                 480

Val Val Arg Gly Pro Gly Phe Thr Gly Gly Asp Xaa Leu Arg Arg Thr
                485                 490                 495

Xaa Xaa Gly Xaa Phe Ala Xaa Xaa Xaa Val Asn Ile Xaa Gly Xaa Leu
            500                 505                 510

Xaa Gln Arg Tyr Arg Xaa Arg Ile Arg Tyr Ala Ser Thr Thr Xaa Leu
        515                 520                 525

Xaa Xaa Xaa Xaa Xaa Xaa Xaa Gly Xaa Xaa Xaa Xaa Xaa Gly Xaa Phe
    530                 535                 540

Xaa Xaa Thr Met Xaa Xaa Gly Asp Xaa Leu Xaa Xaa Xaa Xaa Phe Xaa
545                 550                 555                 560

Xaa Ala Xaa Xaa Xaa Thr Xaa Phe Xaa Phe Xaa Xaa Xaa Gln Ser Xaa
                565                 570                 575

Phe Thr Xaa Gly Xaa Xaa Xaa Phe Xaa Ser Xaa Xaa Glu Val Tyr Ile
            580                 585                 590
```

-continued

```
Asp Xaa Xaa Glu Xaa Xaa Pro Xaa Xaa Xaa Thr Phe Glu Ala Glu Xaa
        595                 600                 605

Asp Xaa Glu Arg Ala Gln Xaa Ala Val Asn Ala Leu Phe Thr Ser Xaa
    610                 615                 620

Xaa Gln Xaa Gly Xaa Xaa Thr Xaa Val Thr Xaa Tyr His Ile Asp Gln
625                 630                 635                 640

Val Ser Asn Leu Val Xaa Cys Leu Ser Asp Glu Phe Cys Leu Asp Glu
                645                 650                 655

Xaa Arg Glu Leu Ser Glu Xaa Val His Xaa Ala Xaa Arg Leu Ser Asp
            660                 665                 670

Xaa Arg Asn Leu Leu Gln Asp Pro Asn Phe Xaa Gly Ile Asn Arg Gln
        675                 680                 685

Xaa Asp Xaa Gly Trp Arg Gly Ser Thr Asp Ile Thr Ile Gln Xaa Gly
    690                 695                 700

Asp Asp Val Phe Xaa Glu Asn Tyr Val Thr Leu Pro Gly Thr Phe Asp
705                 710                 715                 720

Glu Cys Tyr Pro Thr Tyr Leu Tyr Gln Xaa Ile Asp Glu Ser Xaa Leu
                725                 730                 735

Xaa Xaa Tyr Thr Arg Tyr Gln Leu Arg Gly Tyr Ile Glu Asp Ser Gln
            740                 745                 750

Asp Leu Glu Ile Tyr Leu Ile Arg Tyr Asn Xaa Xaa His Glu Pro Val
        755                 760                 765

Asn Val Xaa Gly Thr Gly Ser Leu Trp Pro Leu Ser Val Xaa Xaa Xaa
    770                 775                 780

Ile Xaa Xaa Cys Gly Glu Pro Asn Arg Cys Ala Pro His Leu Glu Trp
785                 790                 795                 800

Asn Pro Asp Leu Xaa Cys Ser Cys Arg Asp Gly Glu Xaa Cys Xaa His
                805                 810                 815

His Ser His His Phe Ser Leu Asp Ile Asp Val Gly Cys Thr Asp Leu
            820                 825                 830

Asn Glu Asp Leu Xaa Val Trp Xaa Ile Phe Xaa Ile Xaa Thr Gln Asp
        835                 840                 845

Gly His Ala Arg Leu Gly Asn Leu Glu Phe Leu Glu Glu Xaa Pro Leu
    850                 855                 860

Xaa Gly Glu Ala Leu Xaa Arg Val Xaa Arg Ala Glu Xaa Xaa Trp Arg
865                 870                 875                 880

Asp Xaa Arg Glu Xaa Leu Xaa Leu Glu Thr Asn Ile Val Tyr Xaa Glu
                885                 890                 895

Ala Xaa Glu Ser Val Asp Ala Leu Phe Val Asn Ser Gln Tyr Asp Xaa
            900                 905                 910

Leu Gln Ala Asp Thr Asn Ile Ala Met Ile His Ala Ala Asp Xaa Arg
        915                 920                 925

Val His Arg Ile Arg Glu Ala Tyr Leu Pro Glu Leu Ser Val Ile Pro
    930                 935                 940

Gly Val Asn Xaa Xaa Ile Phe Glu Glu Leu Xaa Gly Arg Ile Phe Thr
945                 950                 955                 960

Ala Xaa Xaa Leu Tyr Asp Ala Arg Asn Val Ile Xaa Asn Gly Xaa Phe
                965                 970                 975

Asn Asn Gly Leu Xaa Cys Trp Asn Val Xaa Gly His Val Asp Val Glu
            980                 985                 990

Glu Gln Asn Asn His Arg Ser Val Leu Val Val Pro Glu Trp Glu Ala
        995                 1000                1005

Glu Val Ser Gln Glu Val Arg Val Cys Pro Gly Arg Gly Tyr Ile Leu
    1010                1015                1020
```

-continued

```
Arg Val Thr Ala Tyr Xaa Glu Gly Tyr Gly Glu Gly Cys Val Thr Ile
1025                1030                1035                1040

His Glu Xaa Xaa Asn Asn Thr Asp Glu Leu Xaa Phe Ser Asn Cys Xaa
                1045                1050                1055

Xaa Glu Xaa Val Tyr Pro Xaa Asn Thr Val Xaa Cys Asn Asp Tyr Xaa
            1060                1065                1070

Xaa Asn Xaa Xaa Xaa Xaa Xaa Xaa Ala Xaa Xaa Ser Arg Asn Arg Gly
        1075                1080                1085

Tyr Asp Glu Xaa Tyr Xaa Ser Asn Ser Ser Xaa Pro Ala Asp Tyr Ala
    1090                1095                1100

Xaa Val Tyr Glu Glu Xaa Xaa Tyr Thr Asp Gly Xaa Arg Xaa Asn Pro
1105                1110                1115                1120

Cys Glu Xaa Asn Arg Gly Xaa Xaa Xaa Xaa Thr Pro Leu Pro Ala Gly
                1125                1130                1135

Tyr Val Thr Xaa Glu Leu Glu Tyr Phe Pro Glu Thr Asp Xaa Val Trp
            1140                1145                1150

Xaa Glu Ile Gly Glu Thr Glu Gly Thr Phe Ile Val Asp Ser Val Glu
        1155                1160                1165

Leu Leu Leu Met Glu Glu
    1170
```